(12) United States Patent
Claus

(10) Patent No.: US 8,194,949 B2
(45) Date of Patent: Jun. 5, 2012

(54) USER ADJUSTMENT MEASUREMENT SCALE ON VIDEO OVERLAY

(75) Inventor: Michael J. Claus, Newport Coast, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 1165 days.

(21) Appl. No.: 12/021,080

(22) Filed: Jan. 28, 2008

(65) Prior Publication Data
US 2009/0190808 A1   Jul. 30, 2009

(51) Int. Cl.
*G06K 9/00* (2006.01)
(52) U.S. Cl. .................................................. 382/128
(58) Field of Classification Search .............. 382/128, 382/206; 128/922; 702/161
See application file for complete search history.

(56) References Cited

U.S. PATENT DOCUMENTS

| | | | | |
|---|---|---|---|---|
| 4,922,909 A | * | 5/1990 | Little et al. | 600/300 |
| 4,980,763 A | * | 12/1990 | Lia | 348/67 |
| 5,070,401 A | | 12/1991 | Salvati et al. | |
| 5,709,972 A | * | 1/1998 | Cookingham et al. | 430/30 |
| 5,751,341 A | * | 5/1998 | Chaleki et al. | 348/65 |
| 5,782,766 A | * | 7/1998 | Weng et al. | 600/443 |
| 5,967,968 A | * | 10/1999 | Nishioka | 600/117 |
| 7,155,043 B2 | * | 12/2006 | Daw | 382/128 |
| 2001/0027272 A1 | * | 10/2001 | Saito et al. | 600/426 |
| 2003/0160824 A1 | * | 8/2003 | Szumla | 345/769 |
| 2004/0261280 A1 | * | 12/2004 | Znaiden et al. | 33/494 |
| 2006/0269111 A1 | * | 11/2006 | Stoecker et al. | 382/128 |
| 2007/0112433 A1 | * | 5/2007 | Frederick et al. | 623/22.41 |
| 2007/0177783 A1 | * | 8/2007 | Yamada | 382/128 |
| 2008/0201641 A1 | * | 8/2008 | Xie | 715/733 |

FOREIGN PATENT DOCUMENTS

| | | |
|---|---|---|
| EP | 1102211 A2 | 5/2001 |
| KR | 10-2007-0012022 | 1/2007 |
| KR | 10-2007-0016752 | 2/2007 |
| WO | WO 2005-074288 A1 | 8/2005 |

* cited by examiner

*Primary Examiner* — Jason M Repko
*Assistant Examiner* — Shervin Nakhjavan
(74) *Attorney, Agent, or Firm* — Abbott Medical Optics Inc.

(57) ABSTRACT

A method and system for superimposing a ruler on a visual representation of a surgical procedure is presented. The design includes providing a reference object while recording the visual representation of the surgical procedure, scaling the ruler to correspond to the reference object within the visual representation of the surgical procedure, and superimposing the ruler from the scaling on the visual representation for subsequent viewing.

22 Claims, 9 Drawing Sheets

USER ADJUSTMENT MEASUREMENT SCALE ON VIDEO OVERLAY

BACKGROUND OF THE INVENTION

1. Field of the Invention

The present design relates generally to the art of medical instrument systems, and more specifically to utilities for use in determining the size of objects rendered in a video frame by a medical device or instrument.

2. Description of the Related Art

Ophthalmic surgeons often record each surgical procedure performed. Recording typically involves capturing and storing medical instrument parameter settings and surgical microscope video images during the course of the procedure. Users can subsequently replay surgical procedure recordings for viewing. For example in an educational setting, user reviewing the procedure may include students, peer surgeons, and industry personnel. Today, products such as the Surgical Media Center fielded by Advanced Medical Optics provide recording functionality enabling users to create and replay, i.e. view simultaneously, video images synchronized with instrument setting parameters.

Current designs do not allow the user to easily determine the absolute size of an object as recorded in a video frame, image, or stream. Current designs are limited because the video images recorded from surgical microscope mounted cameras typically do not contain information relating the size of objects under observation, i.e. desired for viewing, during replay of the surgical procedure. In addition, current designs are further limited as they may be subjected to a wide variation in sizes of different patients' eyes and in the sizes of surgical tools employed, and differences in the surgical microscope's relative power including the amount of zoom set during the procedure. These limitations result in creating an often difficult, if not impossible, task for the user to determine the size of the object under observation during replay.

Currently, to determine the size of an object observed in a video, surgeons typically introduce an item of known size into the video image as a reference during the procedure. This known reference allows the user to assess and compare the size of objects as compared to the known reference during replay. This method is problematic for surgeons to implement because the surgeon must remember to introduce the known reference into view. Depending on the state of the surgical procedure, proper placement of the known reference may be difficult or impossible to achieve. In the situation where the surgeon successfully positions the known reference, this placement may become inconvenient and impede completing the surgical procedure. The surgeon must also keep the known reference in view of the surgical microscope to form the basis for comparison, a difficult task. Complications arise from the surgeon whose hands are typically occupied with the procedure and unable to hold the reference in place. Further, if the known reference is oriented at a different angle than the observed object, and/or if the known reference must be placed distant from the observed object, it is difficult to perform an accurate relative size measurement.

Based on the foregoing, it would be advantageous to provide a user adjustable measurement scale for use in medical instrument systems that overcomes the foregoing drawbacks present in previously known designs used in the control and operation of medical instrument systems.

SUMMARY OF THE INVENTION

According to a first aspect of the present design, there is provided a method for superimposing a ruler on a visual representation of a surgical procedure is presented. The design includes providing a reference object while recording the visual representation of the surgical procedure, scaling the ruler to correspond to the reference object within the visual representation of the surgical procedure, and superimposing the ruler from the scaling on the visual representation for subsequent viewing.

According to a second aspect of the present design, there is provided a medical device comprising a multimedia data storage device configured to receive visual data during a surgical procedure of the surgical procedure; and a computational utility configured to superimpose a visible ruler at a user-desired location and orientation within the visual data obtained during the surgical procedure. The computational utility is configured to superimpose the visible ruler within the visual data after the visual data has been obtained.

These and other advantages of the present design will become apparent to those skilled in the art from the following detailed description of the invention and the accompanying drawings.

BRIEF DESCRIPTION OF THE DRAWINGS

The present design is illustrated by way of example, and not by way of limitation, in the figures of the accompanying drawings in which.

DETAILED DESCRIPTION OF THE INVENTION

The following description and the drawings illustrate specific embodiments sufficiently to enable those skilled in the art to practice the system and method described. Other embodiments may incorporate structural, logical, process and other changes. Examples merely typify possible variations.

Individual components and functions are generally optional unless explicitly required, and the sequence of operations may vary. Portions and features of some embodiments may be included in or substituted for those of others.

The present design provides the ability to determine the size of various objects presented in each video frame of a video replay of a surgical procedure, thereby enhancing the usefulness of replaying video images. Providing an accurate assessment of the size of any object in the video may enable users to more directly compare the video of one procedure relative to another procedure.

The present design is directed to quickly and accurately assessing the size of various observed objects in a video image, i.e. frames, captured and recorded by a safety critical system such as a medical instrument system, for example a surgical microscope. The present design determines or is useful in determining the absolute size of an object present in the video image. In short, the present design may allow a user to precisely place an adjustable measurement scale, i.e. a visible ruler on a video overlay, on a medical instrument system video image during playback.

The design provides a quick, easy to use, accurate, and reliable measurement mechanism for determining the size of individual observed objects and flexible enough allowing the user to expand, i.e. stretch-to-fit, or compress, i.e. shrink-to-fit, sufficient to scale the present designs ruler to a known sized reference in the video frame. In addition, the present design may allow the user to move and rotate the ruler facilitating comparison to objects present at any position, i.e. location (i.e. point) and orientation (i.e. angular position), in the video image.

It is to be understood that any type of system or software application configured to view or replay video frames, for example an image processing application, may benefit from the design presented herein, and such a design is not limited to a phacoemulsification system, surgical system, or even a medical system. The present design may be implemented in, for example, systems including but not limited to phacoemulsification-vitrectomy systems, vitrectomy systems, dental systems, industrial applications, and aerospace applications.

The present design may employ various interface mechanisms to control the presentation of the visible ruler as a video overlay, or just 'ruler', on a video display device connected to the surgical system or medical instrument, such as via a cathode ray tube or liquid crystal display, monitor device, or other subsystem. It will be discussed herein with a particular emphasis on configuring and positioning the ruler in a medical environment, allowing the user to determine the absolute size of various objects present in a video frame, or frames, as stored in and replayed from the surgical systems video storage device. The present design may include a user interface device to configure, for example show ruler or hide ruler, and control, for example rotate or move the ruler. User interface devices may include but are not limited to a touch screen monitor, trackball, mouse (or other pointing device), keypad, foot pedal switch, and/or a computer monitor.

The present design is intended to provide a reliable, non-invasive, and efficient measurement tool for use in assessing the size of various objects present in the video stream and ultimately to directly compare objects found in different video streams representing separate surgical procedures.

System Example

While the present design may be employed in different environments and applications, it will be discussed herein with a particular emphasis on a medical or hospital environment, where a surgeon or health care practitioner performs. For example, one embodiment of the present design is in or with a phacoemulsification surgical system that comprises an independent graphical user interface (GUI) host module, an instrument host module, a GUI device, and a controller module, such as a foot switch, to control the surgical system.

Figure 1:
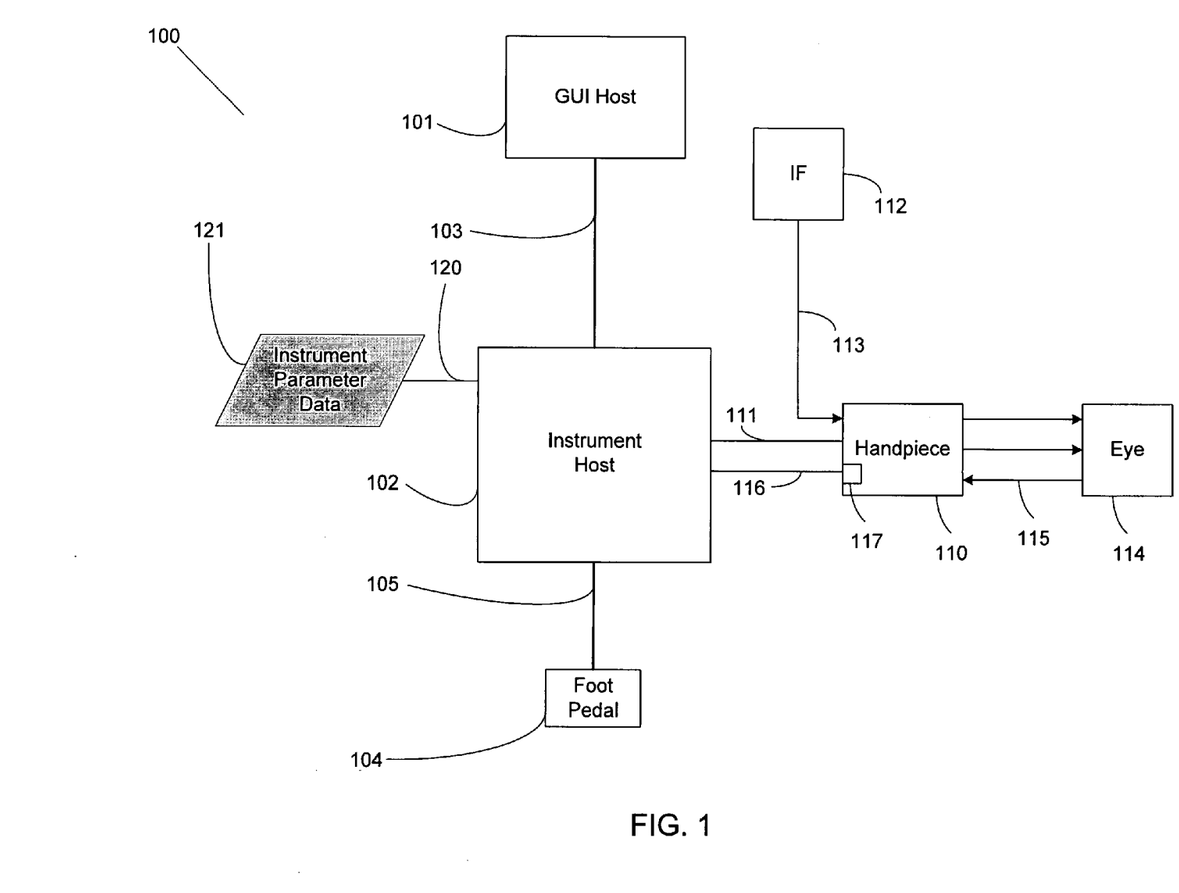
FIG. 1 is a functional block diagram of a phacoemulsification system that may be employed in accordance with an aspect of the present design.

FIG. 1 illustrates an exemplary phacoemulsification/vitrectomy system 100 in a functional block diagram to show the components and interfaces for a safety critical medical instrument system that may be employed in accordance with an aspect of the present design. A serial communication cable 103 connects GUI host 101 module and instrument host 102 module for the purposes of controlling the surgical instrument host 102 by the GUI host 101. Instrument host 102 may be considered a computational device in the arrangement shown, but other arrangements are possible. An interface communications cable 120 is connected to instrument host 102 module for distributing instrument parameter data 121 to other systems, subsystems and modules within and external to instrument host 102 module.

Although shown connected to the instrument host 102 module, interface communications cable 120 may be connected or realized on any other subsystem (not shown) that could accommodate such an interface device able to distribute instrument parameter data 121.

A foot pedal 104 switch module may transmit control signals relating internal physical and virtual switch position information as input to the instrument host 102 over serial communications cable 105. Instrument host 102 may provide a database file system for storing configuration parameter values, programs, and other data saved in a storage device (not shown). In addition, the database file system may be realized on the GUI host 101 or any other subsystem (not shown) that could accommodate such a file system.

The phacoemulsification/vitrectomy system 100 has a handpiece 110 that includes a needle and electrical means, typically a piezoelectric crystal, for ultrasonically vibrating the needle. The instrument host 102 supplies power on line 111 to a phacoemulsification/vitrectomy handpiece 110. An irrigation fluid source 112 can be fluidly coupled to handpiece 110 through line 113. The irrigation fluid and ultrasonic power are applied by handpiece 110 to a patient's eye, or affected area or region, indicated diagrammatically by block 114. Alternatively, the irrigation source may be routed to eye 114 through a separate pathway independent of the handpiece. Aspiration is provided to eye 114 by the instrument host 102 pump (not shown), such as a peristaltic pump, through lines 115 and 116. A switch 117 disposed on the handpiece 110 may be utilized to enable a surgeon/operator to select an amplitude of electrical pulses to the handpiece via the instrument host and GUI host. Any suitable input device, such as for example, a foot pedal 104 switch may be utilized in lieu of the switch 117.

Figure 2:
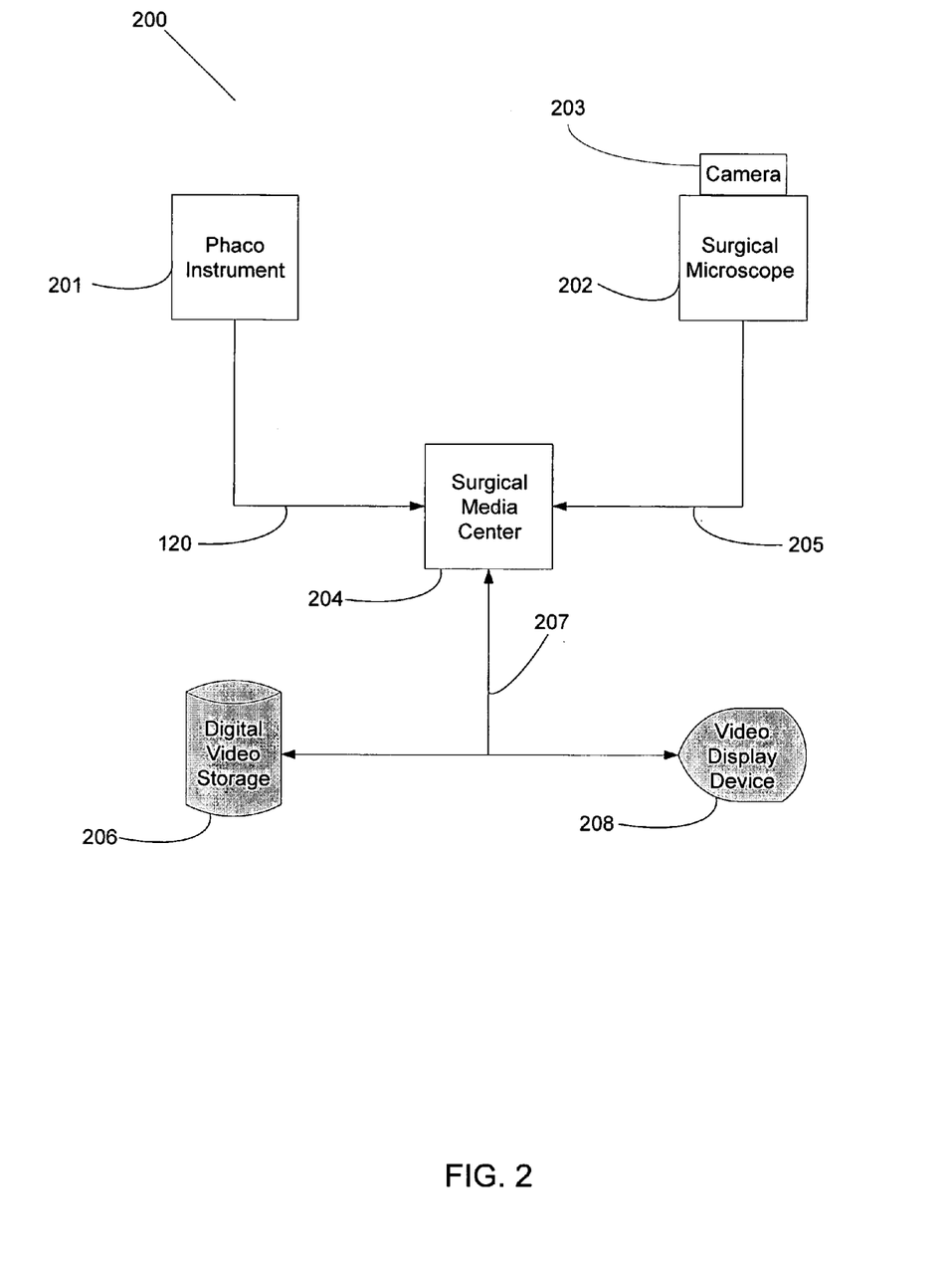
FIG. 2 is a functional block diagram of a surgical system that may be employed in accordance with an aspect of the present design.

FIG. 2 illustrates and exemplary surgical system 200 in a functional block diagram to show the components and interfaces for an image processing safety critical medical instrument with a video recording and playback system that may be employed in accordance with an aspect of the present design. Surgical system 200 may include a surgical instrument, for example a phacoemulsification instrument 201, such as the phacoemulsification/vitrectomy system 100 shown in FIG. 1.

The surgical system 200 may further include a surgical microscope 202 focused on the surgical procedure, e.g. patients eye, and may involve camera 203, or other device suitable for video recording, and may transfer the resulting video data, analog or digital, to surgical media center 204 via communications cable 205. Surgical media center 204 is a processing device that manages the multimedia data recorded by the surgical microscope, and the instrument parameter data 121 in real-time, including but not limited to vacuum, power, flow, and foot pedal position generated from phacoemulsification instrument 201 during the surgical procedure. Managing the multimedia data includes synchronizing the temporal relationship between the instrument parameters and settings data from phaco instrument 201 and the video data from surgical microscope 202. The surgical media center may display the video data with a graphical video overlay showing the corresponding parameters and instrument settings at each instant during the procedure.

The surgical system may further include a digital video storage device 206 configured to store the multimedia data recorded. Video storage device 206 may connect to and be accessed by surgical media center 204 via communications cable 207. In addition, a video display device 203 may connect to the surgical media center 204 and the digital video storage device 206 via communications cable 207.

In this arrangement, surgical system 200 may record a video image of the procedure/surgery and record medical system instrument parameters and settings utilized by the phacoemulsification instrument 201 in real-time. The surgical media center 204 may synchronize instrument data with the video stream allowing simultaneous display of video data with a graphical overlay showing the corresponding parameters and system settings at each instant of the procedure on a frame-by-frame basis. This cumulative data, i.e. the video data synchronized with the setting and parameter data may be stored and archived in digital video storage device 206. During playback, the user may select to show or hide different components of the instrument data rendered on video display device 208.

Adjustable Measurement Scale Utility

The present design may involve a user adjustable measurement scale (AMS) utility configured to place a visible ruler at a user desired location on the video image during playback, for execution by a processing device such as surgical media center 204, for accurate assessment of the size of various objects represented in the video image/stream. The AMS utility may be configured to render the ruler as a graphical video overlay for presentation on a video display device. The AMS utility apparatus and method of the present design for configuring and controlling a visible ruler presented as a graphical video overlay on top of a video image during playback will now be described within an image processing safety critical medical instrument/surgical system.

Figure 3:
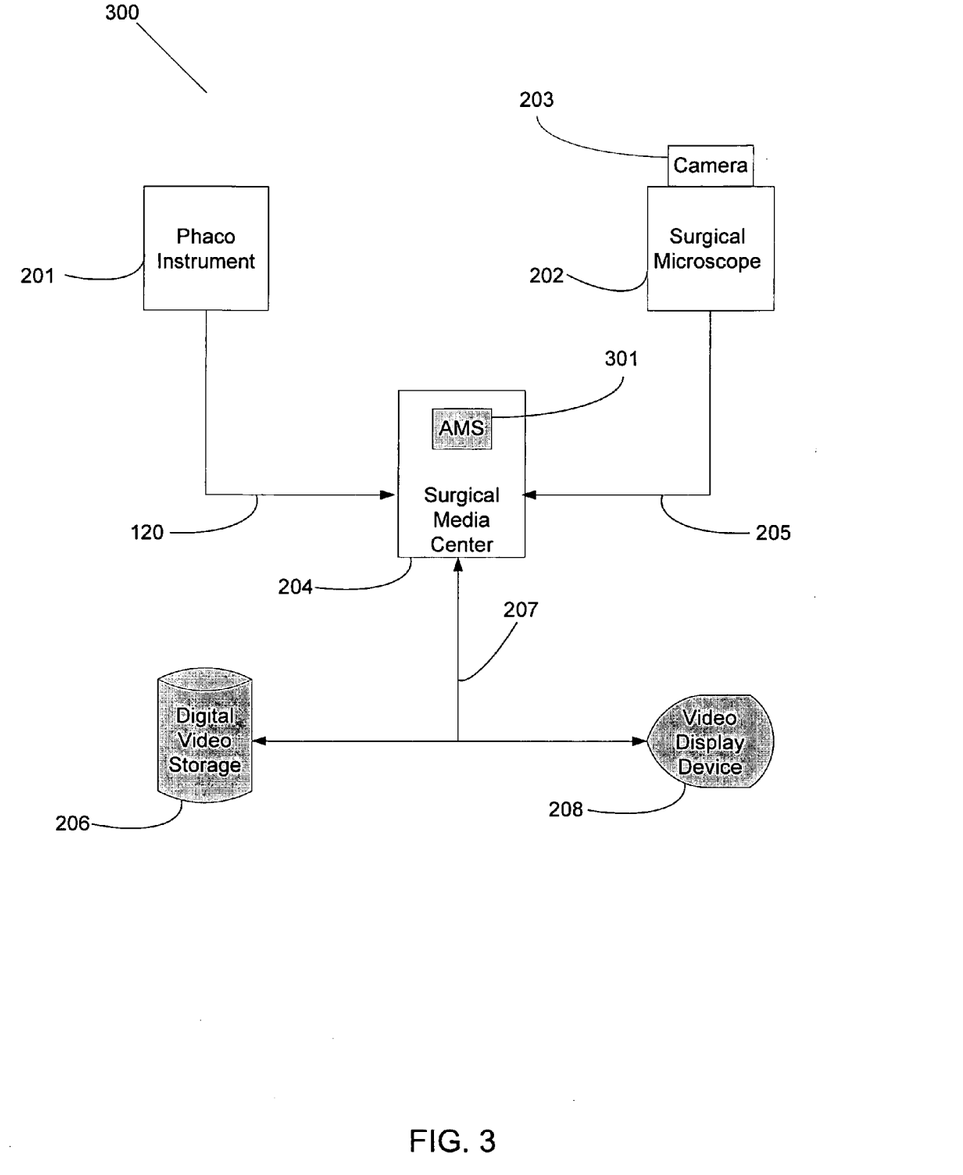
FIG. 3 is a functional block diagram of a surgical system including the present designs ruler functionality that may be employed in accordance with an aspect of the present design.

FIG. 3 illustrates a functional block diagram for a surgical system 300 including the present designs apparatus and method wherein an AMS utility 301 executes within the surgical media center 204 during playback. In this arrangement, the present design is configured to superimpose a visible ruler for use in determining the size of objects present in the recorded video.

The present design may communicate data for playback from digital video storage 206 to AMS utility 301 via communications cable 207. When activated by the user, AMS utility 301 may generate the present design's graphical video overlay for presentation on top of the video data during playback. The graphical video overlay may contain the visible ruler. The resultant graphical video overlay and digital video data, with synchronized instrument parameter data, may be transferred over communication cable 207 to video display device 208 for rendering, and ultimately viewed by the user. Methods for generating a graphical video overlay and superimposing the overlay onto a video frame, image, or stream are generally understood by those skilled in the art.

The digital video storage 206 database file system may store video data generated by a camera 203 mounted on surgical microscope 202 and associated instrument parameter data 121, including instrument settings, wherein the video data is synchronized with the instrument parameter data 121.

Although illustrated as a separate entity, AMS utility 301 may reside within the surgical microscope 202, surgical media center 204, other subsystems, or be realized using external devices and/or software. In addition, the present design may be realized by embedding the software utility in an existing medical instrument system design.

The AMS utility 301 illustrated in FIG. 3 may operate separate from phaco instrument 201 or may be configured to operate as part of phaco instrument 201 or any other subsystem, for example surgical microscope 202 and surgical media center 204. The AMS utility functionality may be realized in hardware, software, firmware, or any combination of processing thereof. Although FIG. 3 illustrates the AMS utility 301 as a single separate entity, i.e. module, process, and mechanism, the present design is not limited to a single separate entity and may be realized by incorporating some or all of the functionality of the present design into multiple separate software entities.

Operation

FIGS. 4 through 8 provide diagrammatic representations of example video screens generated by the adjustable measurement scale utility available for viewing by the user when operating the present design's ruler functionality. For purposes of illustration, handpiece 110 including vibrating unit 410 and switch 117, is shown in FIGS. 4 through FIG. 8 as it may be recorded with eye 414 during the surgical procedure.

Operation of AMS utility 301 assumes that the user, e.g. surgeon, previously performed a surgical procedure that was recorded by surgical system 300 and the data, i.e. the video image of the surgery and the parameters employed by the phacoemulsification system during the surgery, is stored in video data storage 206 ready for playback. During playback of the stored data, the user may configure and control the AMS utility 301 to render the ruler at a desired position for presentation on a video display device in association with, or superimposed on, or on top of the stored data presented.

A user operating the surgical system may provide input to the AMS utility to configure and control how the ruler is displayed via a touch screen, trackball, mouse or other pointing device, or keyboard. For example, configuration may include choosing the measurement unit, e.g. metric or English, setting the number of divisions per measurement unit, i.e. increasing or decreasing the number of rule marks.

Optional configuration items may include but are not limited to choosing the color or colors used to display the visible ruler, selecting whether units are displayed or suppressed, and selecting the scale type, for example including but not limited to linear, exponential or logarithmic forms. In addition the user may configure the style or shape of the ruler presented. For example, the ruler may be arranged in a straight line, or a curved shape sufficient to measure the diameter of a round subject object within the video images. Another particularly useful measurement that can be provided by this ruler is the angle between one object and another, e.g., angle of corneal incision. In these situations, the AMS utility may enable the user to configure the ruler by selecting the desired diameter of the ruler and the desired rate of curvature. The ruler may include or omit lines or measurement indicators as desired, may or may not include numeric values, and may take generally any form that affords the user the ability to judge the size, quality, or physical dimensions of the object being viewed.

Figure 4:
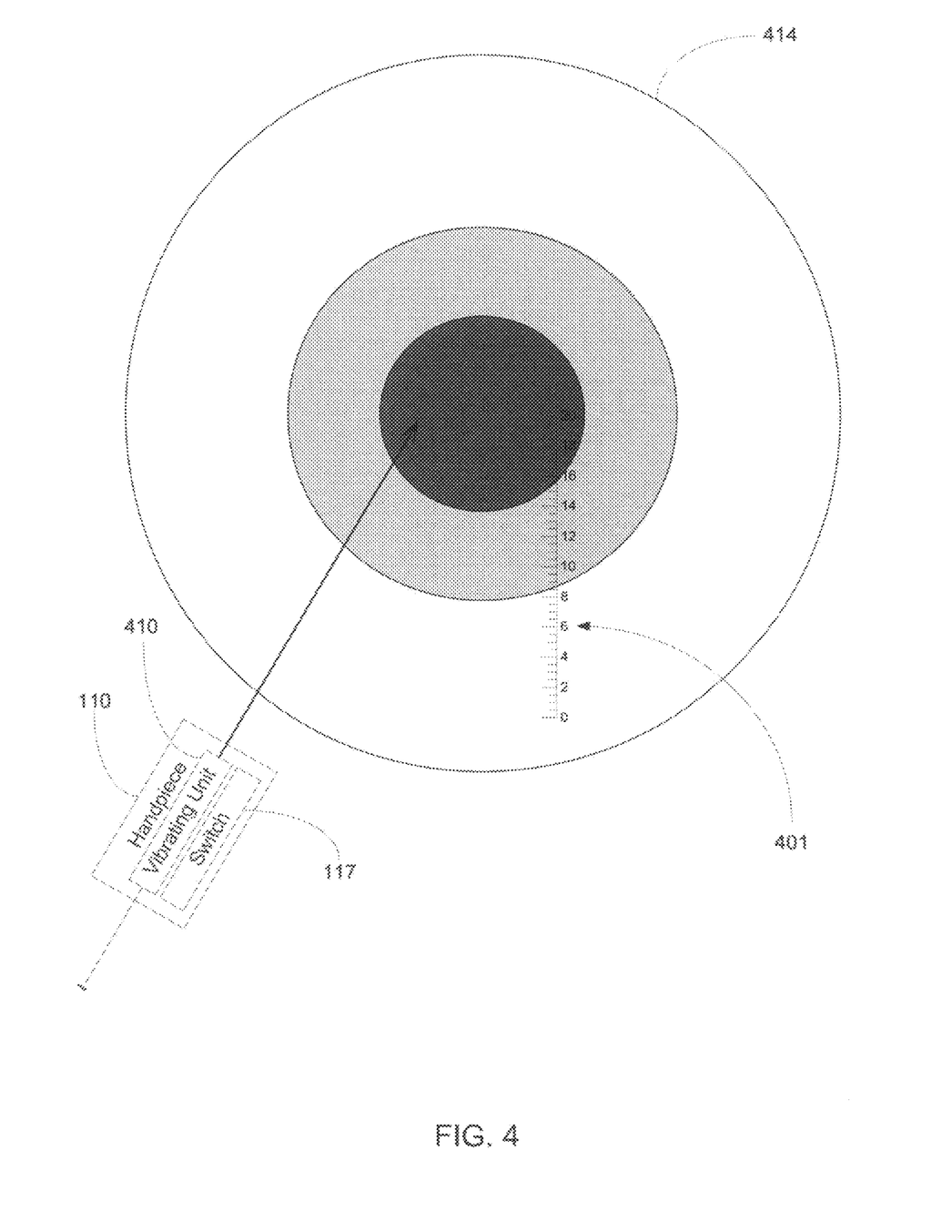
FIG. 4 is a diagram illustrating an example video screen generated by the present design as rendered on video display device for viewing by a user in accordance with an aspect of the present design.

FIG. 4 illustrates an example video screen displaying ruler at 401 generated by the user adjustable measurement scale utility 301 and rendered on video display device 208. The user may provide input during playback to control whether the ruler is shown on top of the video image, i.e. visible, allowing the user to view the ruler during playback as desired as well as at other times.

Figure 5:
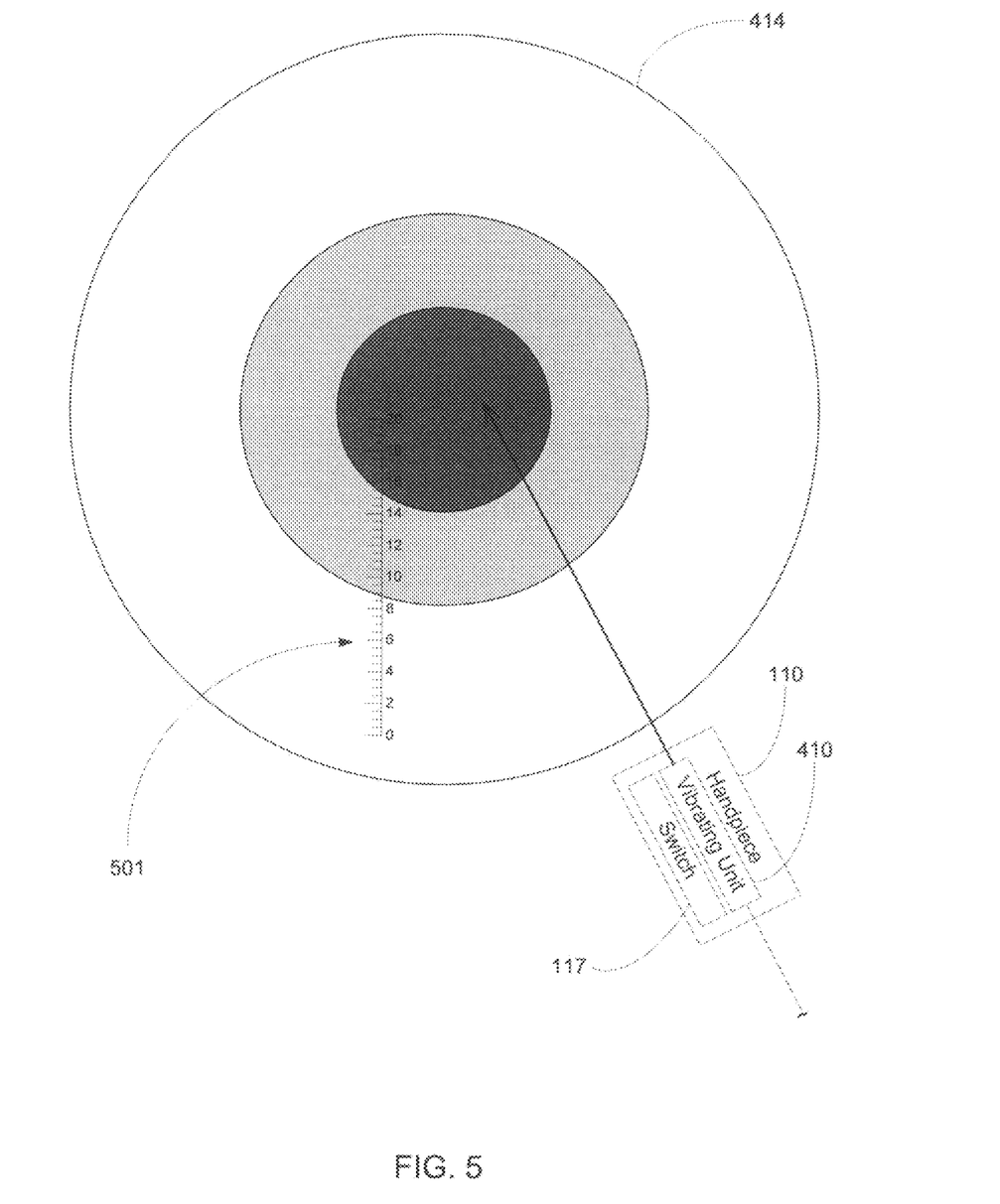
FIG. 5 is an example video screen illustrating placing the user adjustable measurement scale at any location within a video frame as rendered on a video display device for viewing by a user in accordance with an aspect of the present design.
Figure 6:
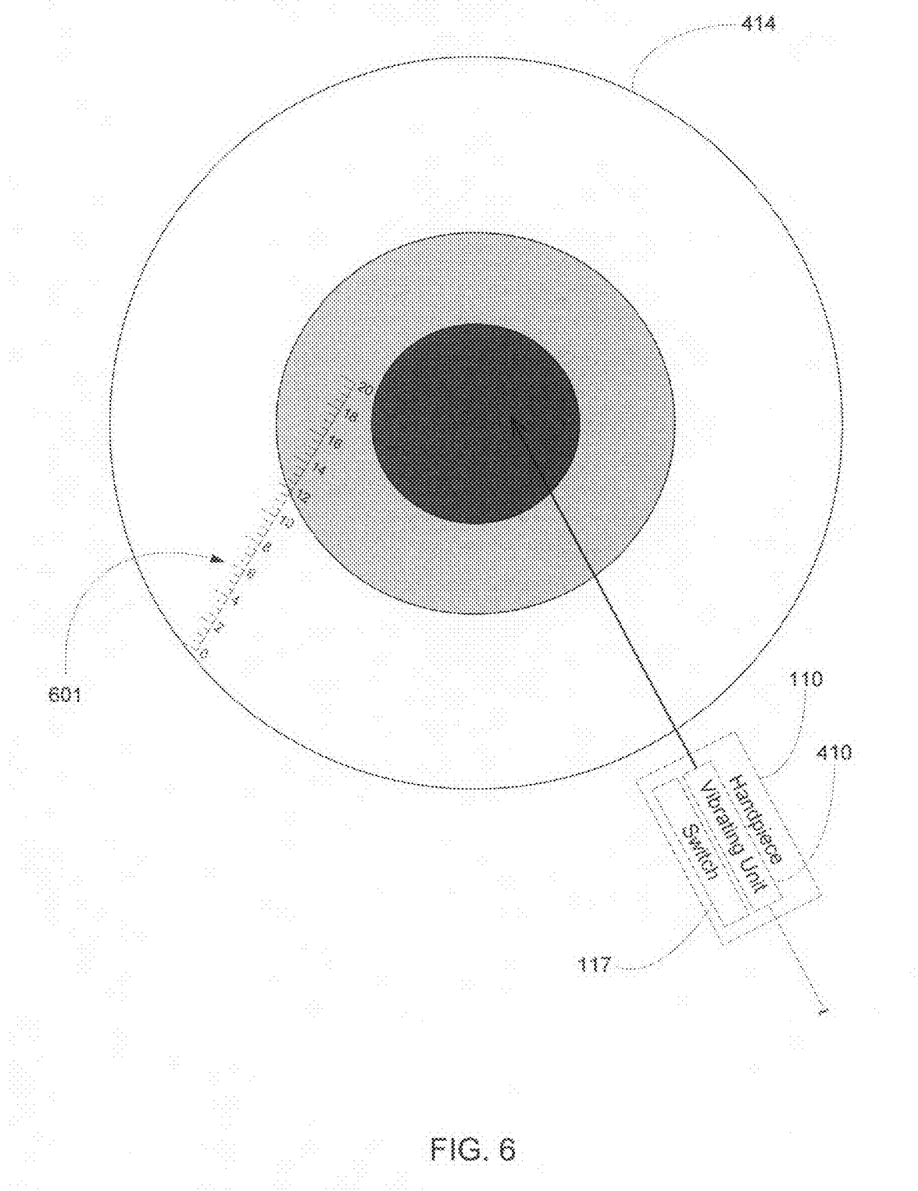
FIG. 6 is an example video screen illustrating rotating the user adjustable measurement scale at any orientation within a video frame as rendered on a video display device for viewing by a user in accordance with an aspect of the present design.

FIG. 5 illustrates an example video screen displaying 'positioning' the ruler at 501 at any location, and FIG. 6 illustrates an example video screen displaying 'rotating' the ruler at 601 at any orientation within a video frame as rendered on video display device 208. The user may provide input during playback to control and place the ruler on the image allowing the user to position the ruler at any desired location and orientation on the video image. In this arrangement, the present design may enable the user to locate and orient the ruler in a position sufficiently close to allow comparisons with various objects observed in the video stream or to scale the ruler (refer to FIGS. 7 and 8). In addition, the user may locate the ruler during replay in a position where it does not interfere with clearly viewing the conduct of the surgical procedure.

Figure 7:
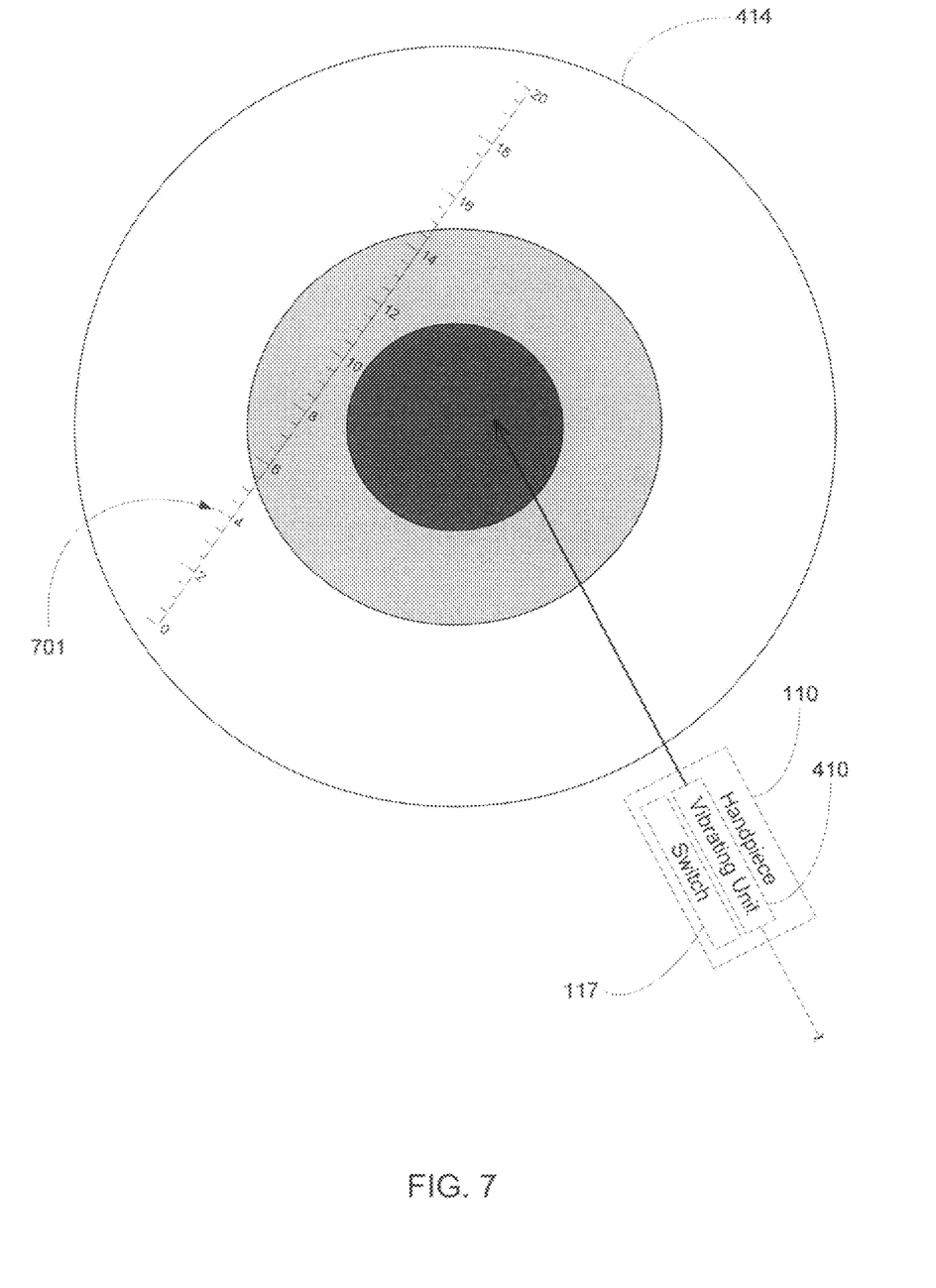
FIG. 7 is an example video screen illustrating expanding the user adjustable measurement scale to any size within a video frame as rendered on a video display device for viewing by a user in accordance with an aspect of the present design.
Figure 8:
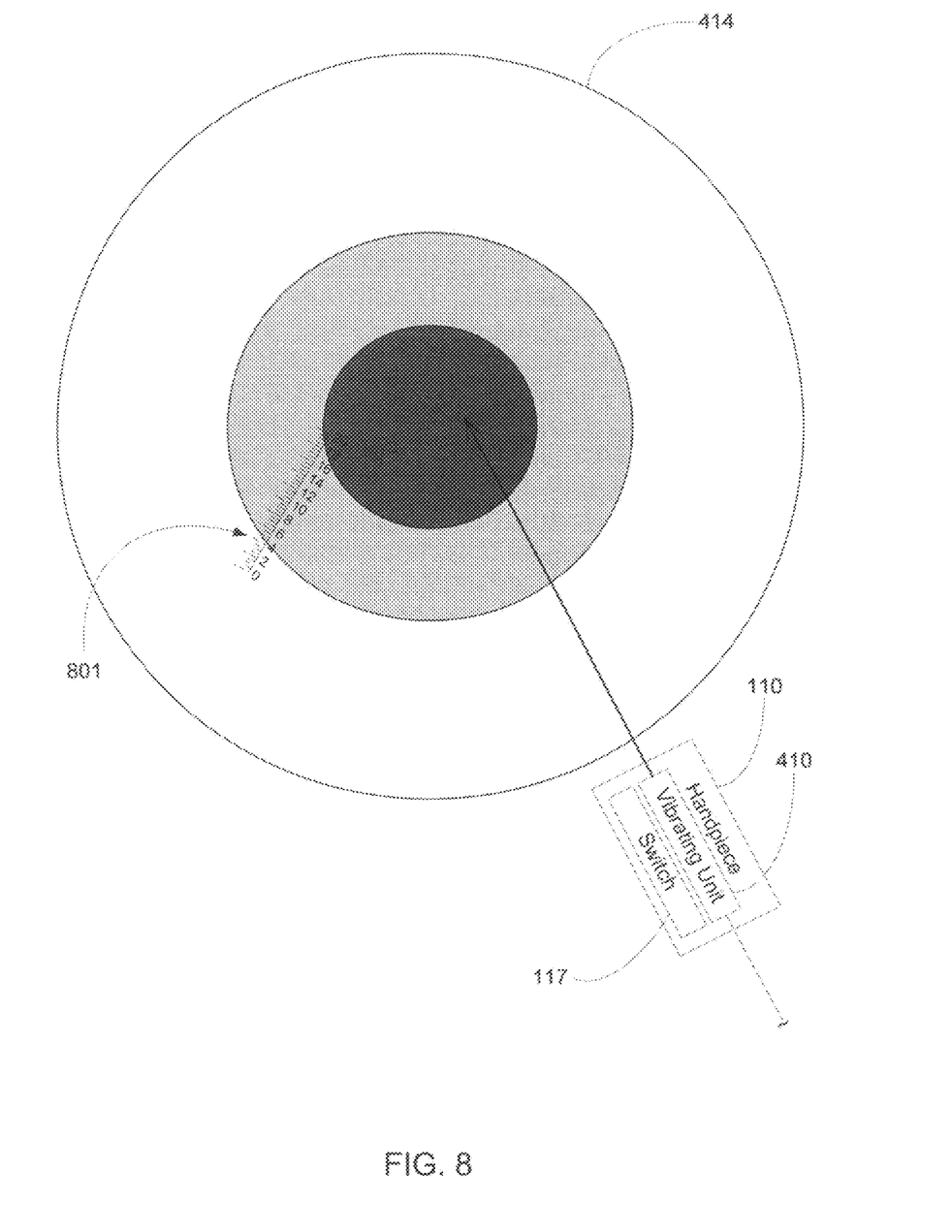
FIG. 8 is an example video screen illustrating compressing the user adjustable measurement scale to any size within a video frame as rendered on a video display device for viewing by a user in accordance with an aspect of the present design.

FIG. 7 illustrates an example video screen displaying 'expanding' the ruler at 701 to any length and FIG. 8 illustrates an example video screen displaying 'compressing' the ruler at 801 to any length within a video frame as rendered on video display device 208. The user may provide input during playback to control and size, e.g. expand or compress, the ruler on the image allowing the user to accurately scale the ruler by sizing the length to match that of a known reference in the video image. In this arrangement, the present design may enable the user to scale the ruler sufficiently to enable accurate assessments for the size of an objects observed in the video stream.

Figure 9:
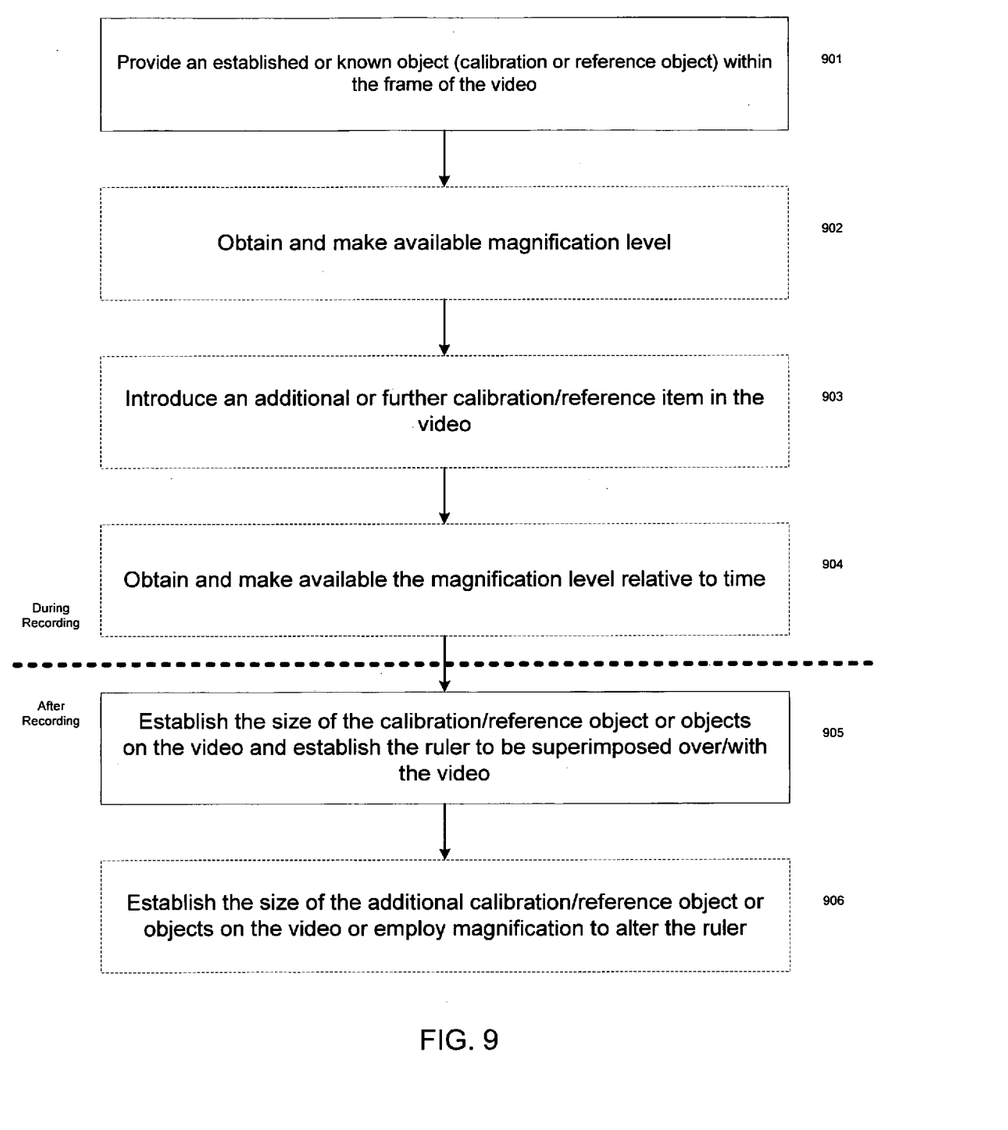
FIG. 9 is a flowchart representing one embodiment of operation of the present design when using at least one reference item or calibration object.

In order to calibrate the ruler, or establish the proper scaling/relationship between objects in the video and the ruler 801, a specific procedure is undertaken that accounts for sizing and changes in magnification, if any, that occur during the surgical procedure. FIG. 9 illustrates an exemplary flowchart of a procedure that may be employed in accordance with the current design to calibrate or establish the relationship between objects in the video and ruler 801. Point 901 represents providing an established or known object in the frame of the video. Any known sizing representative object may be employed as long as the object is either clearly understood or known to persons that may employ the video at a later time. Examples include, but are not limited to, some type of measurement tool such as an actual physical ruler, a medical instrument of known or common dimensions, a medical instrument or other device having two points or components separated by a known distance, a medical supply of a generally known or understood dimension, such as a lens, suture, or other medical product. A common item may be employed, and when working in a sterile environment the item is expected to be sterile, but does not necessarily need to be a medical item. Items such as a writing pen, stylus, small ruler, or other device may be employed if a common or known medical device is unavailable. However, introduction of foreign bodies would likely be kept to a minimum in this environment.

The item employed may be referred to as the calibration item, also called a reference or reference item or object, and the calibration item may be introduced in camera view at the beginning, end, or at any point in the middle of the video. In general, it is preferable to briefly introduce the calibration item into the video and perform the procedure with the calibration item out of the video frame, but it can be maintained in the frame for extended periods of time if desired. As shown at point 902, the magnification level may be obtained when the calibration item is placed in the video frame. If, at a subsequent time during the procedure, the operator or system changes the magnification, the system can account for the magnification change in establishing the ruler 801 described above. Alternately, the same or a different calibration item may be introduced if magnification changes during the surgical procedure. Point 903 illustrates the option to introduce an additional or further calibration item if magnification changes occur or use of an additional calibration item is otherwise desired. It is anticipated that discrete magnification changes may occur while receiving images of the procedure, rather than continuous magnification changes. If continuous or evolving magnification changes occur during the procedure, the system as shown in optional point 904 may obtain and make available the magnification level relative to time such that the ruler 801 can be altered and displayed at an appropriate size once the video has completed. This may also occur if discrete magnifications occur or are expected.

Subsequent to recording the procedure, a user may establish the size of the calibration/reference object or objects on the video at point 905 and may establish a ruler 801 accordingly as discussed above, where the ruler is superimposed or otherwise placed in the frame at a desired position and orientation. For example, if the video shows introduction of a suture (reference) having a length of 0.1 inches, the length of the suture may be established, such as by marking the beginning and end of the suture on the computer system by known graphical techniques and a ruler dimension established and displayed, such as a ruler with dimensions from zero inches to one inch in one-tenth of an inch increments. Display may occur as shown in FIG. 7 or FIG. 8. If the magnification changes and another calibration object is shown, the procedure shown at point 905 may be performed again. Alternately, if magnification values are available, point 906 illustrates a computation may be made relating the magnification to the size of the ruler on screen. Using the aforementioned example of a suture having a known dimension, the magnification employed may be 10×. Once the ruler is established having a range from zero inches to one inch in one-tenth of an inch increments, a change in magnification to 20× would change the ruler sizing that should be displayed, such as to 100 per cent over the previous magnification level. The ruler display would then be from, for example, zero to one-half inch in increments of 0.05 inches when displayed or superimposed on screen.

In this manner, as shown in FIG. 9, the ruler dimensions may be calibrated and established such that the ruler dimensions relative to the region that was recorded, and a ruler such as ruler 801 can be established by an individual that was not present at the procedure at a time after the procedure occurred.

Accurately assessing the size of various observed objects may therefore also enable the user to directly compare and contrast objects found in separate video streams, i.e. individual video streams produced to capture the conduct of a surgical procedure relative to the conduct of the same or similar procedure.

As may be appreciated from FIGS. 4 through 8, the user adjustable measurement scale utility may enable the present design to place the ruler on the video image during playback and allow the user to scale the ruler to known sized reference objects. The user may expand or compress the visible ruler to correctly scale the ruler to a known sized reference object in the video frame. The user may control the scaled ruler by moving and rotating its position sufficient to place the ruler close enough to the object under observation sufficient to allow a comparison to objects at any position and orientation in the video image.

The design presented herein and the specific aspects illustrated are meant not to be limiting, but may include alternate components while still incorporating the teachings and benefits of the invention. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

The foregoing description of specific embodiments reveals the general nature of the disclosure sufficiently that others can, by applying current knowledge, readily modify and/or adapt the system and method for various applications without departing from the general concept. Therefore, such adaptations and modifications are within the meaning and range of equivalents of the disclosed embodiments. The phraseology or terminology employed herein is for the purpose of description and not of limitation.

What is claimed is:

1. A method for determining a size of an object present in a video image, comprising:
   rendering a ruler at a desired position for presentation with recorded visual data; and
   scaling dimensions of said ruler based on a known reference presented in said recorded data;
      wherein said rendering and scaling provide a visual overlay of the ruler in a desired scale atop the visual recorded data; and
   providing at least one magnification related value for a view in a visual representation corresponding to the reference object,
      wherein the ruler changes size when magnification values change during the visual representation of the surgical procedure.

2. The method of claim 1, wherein data comprises a video image of a surgical procedure.

3. The method of claim 1, wherein rendering comprises generating said ruler based on user provided configuration and control input.

4. The method of claim 3, wherein scaling dimensions further comprises setting a ruler measurement unit to quantities represented by one from a group comprising metric and English values.

5. The method of claim 3, wherein scaling dimensions further comprises selecting a number of divisions per measurement unit.

6. The method of claim 3, further comprising electing to display said ruler in situations where said ruler is not elected to be hidden.

7. The method of claim 3, wherein the rendering and scaling comprise moving and rotating said ruler to any orientation within a video frame renderable on a video display device.

8. The method of claim 1, further comprising enabling a user to directly compare object sizes for objects found in separately recorded video data.

9. A medical device comprising:
   a multimedia data storage device configured to receive visual data during a surgical procedure of the surgical procedure; and
   a computational utility configured to superimpose a visible ruler at a user-desired location and orientation within the visual data obtained during the surgical procedure;
   wherein the computational utility is configured to superimpose the visible ruler within the visual data after the visual data has been obtained,
      wherein the visual data comprises a visual representation of a reference object employed to calibrate the ruler superimposed by the computational utility,
   wherein the computational utility is configured to generate at least one magnification related value for a view in the visual representation corresponding to the reference object, and
   wherein the visible ruler changes size when magnification values change during a visual representation of the surgical procedure.

10. The medical device of claim 9, wherein visual data comprises a video image of the surgical procedure together with parameters and settings employed during the surgery.

11. The medical device of claim 9, wherein configuration further comprises setting the measurement unit to metric or English.

12. The medical device of claim 9, wherein the visual data comprises a visual representation of a reference object employed to calibrate the ruler superimposed by the computational utility.

13. The medical device of claim 12, wherein the computational utility employs magnification data for at least one magnification employed during the surgical procedure.

14. The medical device of claim 12, wherein multiple reference object visual representations are employed by the computational utility.

15. A method for superimposing a visible ruler onto an image of a surgical procedure, comprising:
   rendering said ruler as a graphical video overlay superimposed on said image;
   enabling a user to move said ruler to any position in a frame defining a boundary of the image;
   altering ruler size to scale the ruler based on a known sized reference in the image; and
   providing at least one magnification related value for a view in a visual representation corresponding to the known sized reference in the image,
      wherein the ruler changes size when magnification values change during the visual representation of the surgical procedure.

16. The method of claim 15, further comprising orienting said ruler sufficiently close to an object under observation in said video image to accurately assess absolute size of said object.

17. The method of claim 15, wherein altering further comprises setting a ruler measurement unit to quantities represented by one from a group comprising metric and English values.

18. The method of claim 15, wherein altering further comprises providing a number of divisions per measurement unit.

19. The method of claim 15, further comprising electing to display said ruler in situations where said ruler is not elected to be hidden.

20. The method of claim 15, wherein the enabling comprises employing a computational utility to move and rotate said ruler to any orientation within a video frame renderable on a video display device.

21. A method for superimposing a ruler on a visual representation of a surgical procedure, comprising:
   providing a reference object while recording the visual representation of the surgical procedure;

scaling the ruler to correspond to the reference object within the visual representation of the surgical procedure; and superimposing the ruler from said scaling on the visual representation for subsequent viewing, wherein said providing further comprises providing at least one magnification related value for a view in the visual representation corresponding to the reference object, and wherein the ruler changes size when magnification values change during the visual representation of the surgical procedure.

22. The method of claim 21, further comprising providing at least one additional reference object while recording the visual representation and altering the scaling of the ruler to correspond to the at least one additional reference object.

* * * * *

UNITED STATES PATENT AND TRADEMARK OFFICE
CERTIFICATE OF CORRECTION

PATENT NO. : 8,194,949 B2
APPLICATION NO. : 12/021080
DATED : June 5, 2012
INVENTOR(S) : Michael J. Claus It is certified that error appears in the above-identified patent and that said Letters Patent is hereby corrected as shown below:

On the title page, item [54] and column 1, line 1, title should read

USER ADJUSTABLE MEASUREMENT SCALE ON VIDEO OVERLAY

Signed and Sealed this
Twenty-eighth Day of August, 2012

David J. Kappos
*Director of the United States Patent and Trademark Office*